United States Patent [19]

Bertolini

[11] Patent Number: 5,380,710
[45] Date of Patent: * Jan. 10, 1995

[54] PHARMACEUTICAL COMPOSITIONS CONTAINING ACTH (1-24) FOR THE THERAPY OF SHOCK CONDITIONS AND RESPIRATORY AND CARDIOCIRCULATORY INSUFFICIENCES

[76] Inventor: Alfio Bertolini, Via Vittorio Veneto, 8 Scandiano, Italy

[*] Notice: The portion of the term of this patent subsequent to Dec. 27, 2005 has been disclaimed.

[21] Appl. No.: 596,564

[22] Filed: Oct. 11, 1990

Related U.S. Application Data

[63] Continuation of Ser. No. 449,517, Dec. 5, 1989, abandoned, which is a continuation of Ser. No. 310,513, Feb. 14, 1989, abandoned, which is a continuation of Ser. No. 191,726, May 6, 1988, abandoned, which is a continuation of Ser. No. 896,625, Aug. 14, 1986, abandoned.

[30] Foreign Application Priority Data

Aug. 30, 1985 [IT] Italy ................. 22027 A/85

[51] Int. Cl.⁶ ............ A61K 37/00; A61K 37/02
[52] U.S. Cl. ........................... 514/12; 514/13; 530/306; 530/324; 530/325
[58] Field of Search .................. 514/12, 13, 14; 530/306, 324, 325

[56] References Cited

U.S. PATENT DOCUMENTS

| | | | |
|---|---|---|---|
| 3,228,839 | 1/1966 | Kappeler et al. | 514/13 |
| 3,352,844 | 11/1967 | Boissonnas et al. | 530/306 |
| 3,632,743 | 1/1972 | Geller et al. | 530/306 |
| 4,112,073 | 9/1978 | Ono et al. | 530/306 |
| 4,113,858 | 9/1978 | Hashim | 514/13 |
| 4,410,511 | 10/1983 | de Wied et al. | 514/13 |
| 4,594,329 | 6/1986 | Vale Jr. et al. | 530/306 |
| 4,794,103 | 12/1988 | Bertolini | 514/12 |
| 4,794,104 | 12/1988 | Bertolini | 514/13 |
| 5,013,721 | 5/1991 | Melchioni et al. | 514/13 |

OTHER PUBLICATIONS

Felber et al, "Administration by Nasal Spray of an 18 amino acid synthetic polypeptide with corticotropic action," Experientia vol. 25, No. 11, pp. 1195–1196, 1969.

Resusiscitation, 18 (1989). pp. 145–147; pp. 149–150,; pp. 321–326 Elsevier Scientific Publishers Ireland Ltd.

*Primary Examiner*—Michael G. Wityshyn
*Assistant Examiner*—Abdei A. Mohamed
*Attorney, Agent, or Firm*—Walter H. Schneider

[57] ABSTRACT

Pharmaceutical compositions containing ACTH(1-24) are effective in the treatment of shock conditions and of respiratory and cardiocirculatory insufficiency. The compositions of the invention may be administered by parenteral or inhalatory route at a dosage ranging from 1 to 10 mg of active principle.

4 Claims, 2 Drawing Sheets

PHARMACEUTICAL COMPOSITIONS CONTAINING ACTH (1-24) FOR THE THERAPY OF SHOCK CONDITIONS AND RESPIRATORY AND CARDIOCIRCULATORY INSUFFICIENCES

This is a continuation of application Ser. No. 449,517 filed Dec. 5, 1989, now abandoned, which is continuation of application Ser. No. 310,513 filed Feb. 14, 1989, now aband., which is a continuation of application Ser. No. 191,726 filed May 6, 1988, now aband., which is a continuation of application Ser. No. 896,625 filed Aug. 14, 1986, now aband.

The present invention refers to pharmaceutical compositions for the treatment of shock conditions and of respiratory and cardiocirculatory insufficiencies, comprising ACTH (1-24) as the active principle, as well as to the use of said compound for the preparation of medicaments having the above mentioned activities.

ACTH (1-24) is a synthetic polypeptide comprising, in the same sequence characterizing the adrenocorticotropic hormone, the first 24 amino acids out of 39 constituing natural ACTH.

The relationship between the sequence of the amino acids of ACTH and of ACTH (1-24) is therefore the following (the common fragment of the sequence is between the brackets):

[Ser-Tyr-Ser-Met-Glu-His-Phe-Arg-Trp-Gly-Lys-
Pro-Val-Gly-Lys-Lys-Arg-Arg-Pro-Val-Lys-Val-
Tyr-Pro]Asp-Ala-Gly-Glu-Asp-Gln-Ser-Ala-Glu-
Ala-Phe-Pro-Leu-Glu-Phe

The previously known therapeutic uses of ACTH (1-24) concern the treatment of insufficient response of the corticoadrenal gland to the administration of ACTH by intramuscular route and as a coadjuvant in oncology.

There is no relationship between the previously known applications of ACTH (1-24) and those according to the present invention, as it will be evident to anyone skilled in the art, taking also into account the experimental data hereinafter reported. Moreover, while the known uses require a dosage of about 3-4 $\mu$g of ACTH (1-24) per kg body weight (the unit dosage form presently commercially available is in fact a vial containing 0.25 mg of active principle), the novel uses according to the invention require a dose about 20 times higher and, therefore, the use of unit dosage forms containing a proportionally higher amount of the active principle.

As it is well-known, the shock is a clinical condition essentially characterized by an insufficient tissue perfusion, with usually serious hypotension which, if not treated, is generally fatal. Shock may be caused by different causes, such as serious hemorrhages, cranial trauma, dangerous cardiac insufficiency as in certain myocardial infarcts, anaphylactic reactions, etc.

The therapy used at the present time, which is not suited for all kinds of shock, turns out to be unsatisfactory.

Generally, in all shock conditions, there is a tendency to restore the blood volume by means of blood, plasma, saline or glucose solutions or plasma substituents infusion; or to administer oxygen.

However, in serious shock conditions, said treatment is usually unsufficient if not even counteracting. In fact, in the cardiogenic shock, infusion of liquids will overload the heart, whose function is already seriously impaired because of the unsufficient myocardial contractility. Administration of vasoconstrictor drugs, such as noradrenaline, adrenaline, metaraminol, mephentermine, in order to increase pressure, often causes the opposite effect, since, under shock conditions (with the exclusion of the neurogenic shock) a severe sympathetic reflex vasoconstriction is already present, whereby tissular perfusion would be further impaired.

On the contrary, administration of drugs such as dopamine, dobutamine, isoproterenol, glucagon, etc. which improve cardiac inotropism without substantially increasing the peripheral resistances, is preferred, particularly in case of cardiogenic shock.

On the other hand, in some instances, administration of vasodilating drugs such as nitroprussiate and $\alpha$-blockers may be convenient, in order to improve tissue perfusion.

Notwithstanding corticosteroids are widely used in the treatment of shock, no convincing proofs are available supporting the effectiveness of said drugs.

Recently, the efficacy of naloxone in different models of shock has been also studied. Although naloxone turned out to be effective in restoring normal blood pressure values, it is absolutely contraindicated in the shock due to overdose. It is in fact known that naloxone administration to narcotic addicted subjects is followed by a typical abstinence syndrome.

Now it has been surprisingly found that the use of ACTH (1-24) is dramaticaly effective in the therapeutic treatment of shock (hypovolemic, cardiogenic, traumatic, toxic and anaphylactic shocks), cardiovascular collapse, acute hypotension and respiratory insufficiency, independently from the traumatic, psychogenic, toxic, drug overdose causes.

For instance, in the hypovolemic shock, which is always fatal when the blood loss exceeds 50% of the total blood volume, ACTH (1-24) is able to restore to the normal values cardiac output, arterial pressure and breath frequency and amplitude. This effect starts to appear already a few minutes after intravenous injection, it reaches the maximum within 15-20 minutes, it is dose-dependent and require no simultaneous infusion of blood or plasma substitutes.

Even when used as analeptic, ACTH (1-24) shows remarkable advantages in comparison with known analeptics. In fact, all the up to now available analeptics are convulsivant agents used at sub-convulsive dosages, and therefore with a very low therapeutic index and poor handling characteristics; moreover, ACTH (1-24) normalizes the circulatory and respiratory functions if they are depressed, without changing them when they are normal.

ACTH (1-24) is substantially non-toxic.

An object of the present invention is therefore provided by the use of ACTH (1-24) for the preparation of a medicament for the therapeutic treatment of shock conditions and of respiratory and circulatory insufficiencies.

Administration of ACTH (1-24) will be preferably carried out by the intravenous route and by nasal inhalation when ACTH (1-24) is used as an analeptic.

In any case, it has been found that the therapeutically effective dose is comprised from about 80 to about 100 $\mu$g of ACTH (1-24) per kg body weight.

It has been already pointed out that said doses are about 20 times higher than the therapeutically effective ones used for the already known uses of ACTH (1-24).

Thus, a suitable pharmaceutical composition to be administered parenterally, in form of a unit dosage, will comprise from about 1 to about 10 mg of ACTH (1–24) and a pharmacologically acceptable excipient.

In view of the chemical nature of ACTH (1–24), the above mentioned composition will be generally extemporaneously prepared by the physician or by the patient. The commercially available pharmaceutical form will be therefore a preparation in unit dosage form comprising a vial containing from about 1 to about 10 mg of ACTH (1–24) and a vial containing a pharmaceutically acceptable solvent for ACTH (1–24).

When used as an analeptic for the treatment of respiratory and cardiocirculatory insufficiencies the pharmaceutical composition according to the invention will be in an appropriate form for administration by the inhalatory route, for example as a nasal spray, and it will therefore comprise a therapeutically effective amount of ACTH (1–24) and a gaseous or vaporizable pharmaceutically acceptable excipient. The choice of the most suitable excipients is within the skilled in the art's reach.

The effectiveness of ACTH (1–24) in the treatment of shock has been confirmed by several tests on animals and by clinical studies. Some of said tests and the obtained results are reported hereinafter.

TESTS ON EXPERIMENTAL ANIMALS

Intact and adrenalectomized female Wistar rats (Nossan, Correzzano, Milano, Italy) weighing 250 to 300 g, and intact male Beagle dogs (S. Morini, S. Polo d'Enza, Reggio Emilia, Italy) weighing 10 to 12 kg were used. Following anesthetization and heparinization a common carotid artery and an iliac vein were cannulated in rats, while in dogs a femoral artery and vein were used. Arterial blood pressure was recorded by means of a pressure transducer (Statham P23 Db) connected to a polygraph (Battaglia-Rangoni, Bologna, Italy). In some rats, trachea was cannulated and respiration was recorded by means of a transducer (Statham 10272) connected to the same polygraph. Hypovolemic shock was produced by intermittently withdrawing blood from the venous catheter until mean arterial pressure fell to 16–30 mm Hg. In rats, the volume of blood removed was 2–2.5 ml per 100 g of body weight and approximated to, or even exceeded, 50% of the estimated total blood volume; in dogs, the volume of blood removed was 50–60 ml per kg of body weight. Following bleeding and mean blood pressure stabilization in the range of 16–30 mm Hg, animals were given intravenous bolus of either ACTH (1–24) or naloxone.HCl. Control animals were intravenously injected with the same volume of saline (0.1 ml/100 g and 0.2 ml/kg of body weight in rats and dogs respectively). In a set of experiments, in intact rats, 4 μl of ACTH (1–24) or saline were microinfused into a brain lateral ventricle through a previously implanted permanent cannula, at the rate of 0.1 μl/20 sec. The blood pressure was recorded for 2 hours after treatment. In FIGS. 1–8 some representative recordings are reported, while Table 1 shows the data from some tests.

From the examination of the recordings and data it is evident that the intravenous injection of ACTH (1–24) dose-dependently restores blood pressure and pulse amplitude, the effect starting within a few minutes, gradually increasing, and reaching a maximum in 15–30 minutes. All rats intravenously injected with the same volume of saline died after 20.83±2.71 minutes. The dose of 160 μg/kg i.v. of ACTH (1–24) completely restored blood pressure, while the lowest dose used (40 μg/kg i.v.) increased mean arterial pressure by 22 mm Hg within 30 minutes. In the same conditions, a dose of 1 mg/kg i.v. of naloxone.HCl completely restored blood pressure within 30 minutes. The same results were obtained by injecting ACTH (1–24) in adrenalectomized rats, as well as by injecting ACTH (1–24) into a brain lateral ventricle at doses in the range of 6–24 μg/rat. Similar results were obtained in dogs, the intravenous dose of 100 μg/kg of ACTH (1–24) causing an increase of 52 mm Hg within 30 minutes. The intravenous or intracerebroventricular injection of ACTH (1–24) in normal rats had no effect on blood pressure. Both intravenous and intracerebroventricular injections of ACTH (1–24) also dramatically improved the respiratory function, which was severely depressed after bleeding.

The results from this study demonstrate that ACTH (1–24) increases blood pressure and reverses otherwise fatal hypovolemic shock resulting from massive bleeding, in rats and dogs. This effect is not mediated by adrenals, because it is neither abolished nor reduced by adrenalectomy. Yet, it seems to be, at least at a large extent, a central effect, since it can be obtained by the intracerebroventricular injection of ACTH (1–24) at doses that are uneffective when intravenously injected.

Although it is not intended neither necessary to rely on any theoretical interpretation to explain the therapeutic effectiveness of ACTH (1–24) in the applications of the present invention, the obtained results, showing that ACTH (1–24) is even more active than naloxone in reversing shock, and that its action is very probably at the CNS level, are consistent with the hypothesis that melanocortins are endogenous antagonists of opioids, and give further experimental support to the suggested existence of a melanocortin—opioid peptidergic system, with a wide functional meaning and with homeostatic, regulatory roles in many, important functions of the body.

In the light of the present results, the hypothesis that shock, rather than the consequence of a massive activation of endogenous opioid system, is the final effect of the melanocortin-opioid homeostasis with prevalence of the opioid component, should be formulated.

With reference to the diagrams illustrate in the drawings.

TABLE 1

Figure 1:
FIG. 1 shows the effect of ACTH (1–24) (c), 80 μg/kg i.v. on the blood pressure after serious hypotension induced by bleeding in the intact rat.
Figure 2:
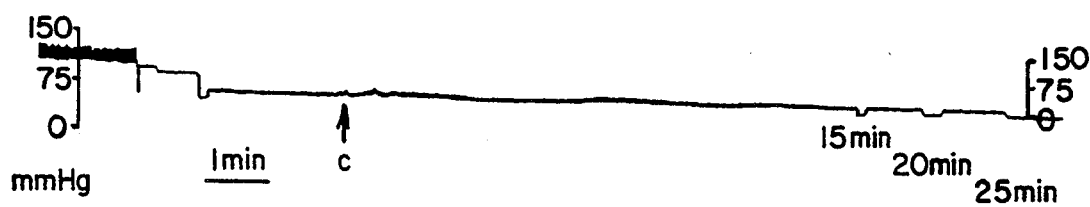
FIG. 2 shows the effect of a saline solution (s), 0.1 ml/100 g body weight, on the blood pressure after serious hypotension induced by bleeding in the intact rat.
Figure 3:
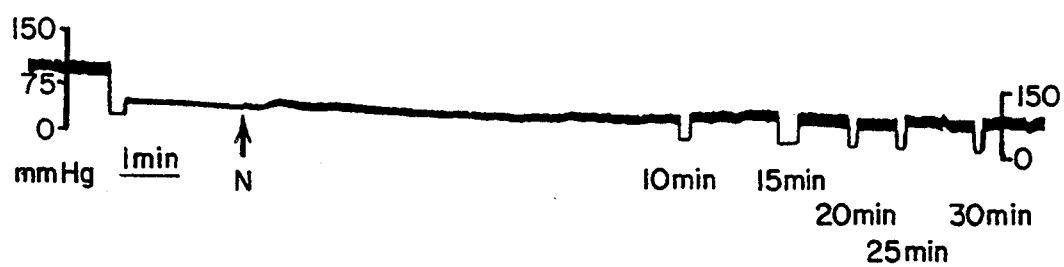
FIG. 3 shows the effect of naloxone (N), 1 mg/kg i.v. on the blood pressure after seriuos hypotension induced by bleeding in the intact rat.
Figure 4:
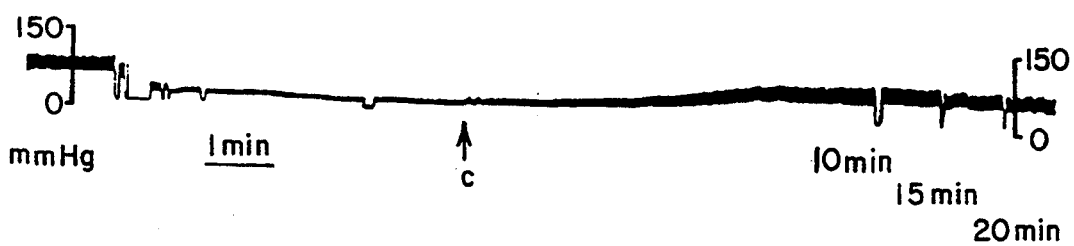
FIG. 4 shows the effect of ACTH (1–24), (c), 80 μg/kg i.v. on the blood pressure after serious hypotension induced by bleeding in the adrenalectomized rat.
Figure 5:
FIG. 5 shows the effect of ACTH (1–24), (c), 24 μg/rat i.c.v. (in the lateral ventricle) on the blood pressure after serious hypotension induced by bleeding.
Figure 6:
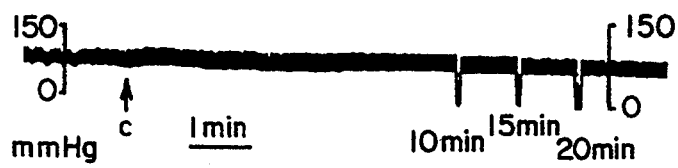
FIG. 6 shows the effect of ACTH (1–24), (c), 160 μg/kg i.v. on the normal blood pressure in the intact rat.
Figure 7:
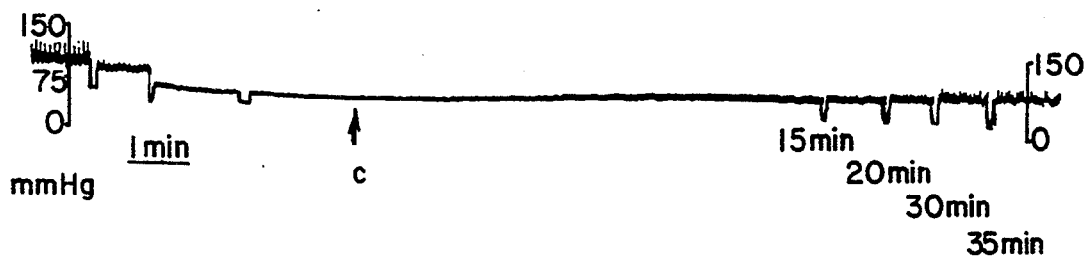
FIG. 7 shows the effect of ACTH (1–24),(c), 100 μg/kg i.v. on the blood pressure after serious hypotension induced by bleeding in the intact dog.
Figure 8:
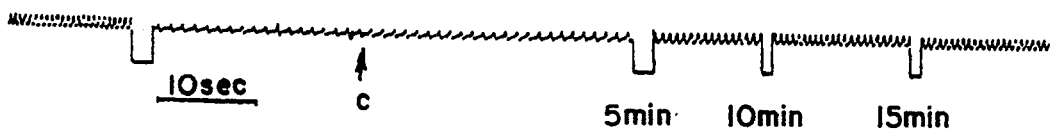
FIG. 8 shows the effect of ACTH (1-24), (c), 80 μg/kg i.v. on the respiratory frequence after serious respiratory insufficiency induced by bleeding in the intact rat.

Effect of ACTH-(1-24), naloxone and saline treatment on mean arterial pressure, respiratory rate and survival, following severe hypotension induced by bleeding.

| Animals* | Treatment° after bleeding | before bleeding | after bleeding | 15-30 min. after treatment | No. of deaths 60 min. after treatment |
|---|---|---|---|---|---|
| | | Mean arterial pressure (mm Hg; $\bar{m} \pm$ S.E.): | | | |
| Intact rats (6) | Saline i.v. | 74,75 ± 9,30 | 18,50 ± 3,12$^\Delta$ | 20,50 ± 2,02 | 6 |
| Intact rats (6) | ACTH-(1-24), 160 μg/kg i.v. | 84,25 ± 13,57 | 24,50 ± 3,77$^\Delta$ | 73,75 ± 8,93 | 0 |
| Intact rats (6) | ACTH-(1-24), 80 μg/kg i.v. | 78,50 ± 9,80 | 18,87 ± 3,18$^\Delta$ | 58,20 ± 7,45 | 0 |
| Intact rats (6) | ACTH-(1-24), 40 μg/kg i.v. | 82,33 ± 11,73 | 17,40 ± 2,68$^\Delta$ | 39,40 ± 9,32 | 0 |
| Intact rats (5) | Naloxone.HCl, 1 μg/kg i.v. | 64,60 ± 4,70 | 22,00 ± 3,15$^\Delta$ | 58,20 ± 6,12 | 0 |
| Adrenalectomized rats (7) | Saline i.v. | 64,29 ± 10,37 | 17,71 ± 2,88$^\Delta$ | 22,00 ± 4,28 | 6 |
| Adrenalectomized rats (8) | ACTH-(1-24), 160 μg/kg i.v. | 64,63 ± 7,70 | 21,88 ± 3,94$^\Delta$ | 50,25 ± 6,33 | 0 |
| Adrenalectomized rats (6) | ACTH-(1-24), 80 μg/kg i.v. | 78,67 ± 14,71 | 17,00 ± 1,53$^\Delta$ | 41,67 ± 5,67 | 0 |
| Adrenalectomized rats (6) | ACTH-(1-24), 40 μg/kg i.v. | 84,33 ± 13,93 | 18,67 ± 1,20$^\Delta$ | 31,67 ± 4,94 | 0 |
| Intact rats (4) | Saline i.c.v. | 91,25 ± 12,39 | 18,00 ± 1,58$^\Delta$ | 24,00 ± 2,48 | 4 |
| Intact rats (4) | ACTH-(1-24), 24 μg/rat i.c.v. | 88,67 ± 11,67 | 17,33 ± 0,67$^\Delta$ | 67,00 ± 8,01 | 0 |
| Intact rats (4) | ACTH-(1-24), 12 μg/rat i.c.v. | 85,00 ± 8,19 | 15,67 ± 3,18$^\Delta$ | 50,67 ± 9,61 | 0 |
| Intact rats (4) | ACTH-(1-24), 6 μg/rat i.c.v. | 85,67 ± 8,56 | 18,33 ± 2,03$^\Delta$ | 37,67 ± 4,18 | 0 |
| Intact rats (4)• | Saline i.v. | 88,30 ± 7,95 | | 91,25 ± 6,35 | |
| Intact rats (4)• | ACTH-(1-24), 160 μg/kg i.v. | 86,50 ± 9,22 | | 89,50 ± 8,81 | |
| Intact rats (4)• | Saline i.c.v. | 80,35 ± 11,60 | | 86,00 ± 6,45 | |
| Intact rats (4)• | ACTH-(1-24), 24 μg/rat i.c.v. | 79,65 ± 8,21 | | 84,19 ± 9,40 | |
| Intact dogs (3) | Saline i.v. | 103,25 ± 7,65 | 23,15 ± 4,50$^\Delta$ | 26,00 ± 6,55 | 3 |
| Intact dogs (3) | ACTH-(1-24), 100 μg/kg i.v. | 105,50 ± 8,35 | 19,30 ± 6,75$^\Delta$ | 71,48 ± 11,20 | 0 |
| | | Respiratory rate (breaths/min.: $\bar{m} \pm$ S.E.): | | | |
| Intact rats (5) | ACTH-(1-24), 80 μg/kg i.v. | 110,25 ± 5,16 | 50,18 ± 4,20$^\Delta$ | 102,12 ± 5,25 | 0 |
| Intact rats (5) | ACTH-(1-24), 24 μg/rat i.c.v. | 106,12 ± 6,22 | 48,14 ± 3,25$^\Delta$ | 100,22 ± 6,88 | 0 |

*In parentheses the number of animals used.
°i.v. = intravenously, i.c.v. = into brain lateral ventricle. •Rats not subjected to bleeding. $^\Delta$P < 0.02, at least, versus value before bleeding and P < 0.05, at least, versus value after bleeding (Student's t-test for paired data).

I claim:

1. A method of therapeutically treating a subject, suffering from any of hypovolemic, cardiogenic, traumatic, toxic and anaphylactic shock or cardiocirculatory and respiratory insufficiencies which comprises administering to said subject a composition comprising ACTH-(1-24) as the principal active ingredient in a unit dosage of about 80-100 μg. per kg. of body weight of said subject in admixture with a pharmaceutically acceptable carrier.

2. A method according to claim 1 in which administration is parenteral for the treatment of shock.

3. A method according to claim 2 in which the composition is in unit dosage form comprising 1-10 mg. of ACTH (1-24).

4. A method according to claim 1 in which administration is inhalatory for the treatment of cardiocirculatory and respiratory insufficiencies.

* * * * *